United States Patent

Wada et al.

[11] Patent Number: 5,803,951
[45] Date of Patent: Sep. 8, 1998

[54] GAS CHROMATOGRAPH AND METHOD OF OPERATING SAME

[75] Inventors: Toyohito Wada, Sagamihara; Kazuya Nakagawa, Kyoto; Satoru Miyoshi, Kyoto; Hiroyuki Tsujiide, Kyoto, all of Japan

[73] Assignee: Shimadzu Corporation, Kyoto, Japan

[21] Appl. No.: 826,623

[22] Filed: Apr. 3, 1997

[30] Foreign Application Priority Data

Apr. 3, 1996 [JP] Japan ................................. 8-108477

[51] Int. Cl.$^6$ .................................................. B01D 15/08
[52] U.S. Cl. ...................... 95/22; 95/82; 95/87; 96/102; 96/105
[58] Field of Search .................. 95/19, 22, 82, 95/87, 89; 96/101–108, 105

[56] References Cited

U.S. PATENT DOCUMENTS

| | | | |
|---|---|---|---|
| 3,496,702 | 2/1970 | Carel et al. | 96/101 X |
| 3,581,465 | 6/1971 | Haruki et al. | 96/101 X |
| 3,668,834 | 6/1972 | Deans | 96/102 X |
| 3,881,892 | 5/1975 | Gehrke et al. | 96/103 X |
| 4,038,053 | 7/1977 | Golay | 96/103 |
| 4,650,499 | 3/1987 | Scott | 96/101 X |
| 4,732,581 | 3/1988 | Cheh et al. | 95/87 |
| 4,976,750 | 12/1990 | Munari | 96/102 X |
| 5,094,741 | 3/1992 | Frank et al. | 96/101 X |
| 5,108,466 | 4/1992 | Klein et al. | 96/102 X |
| 5,242,471 | 9/1993 | Markham et al. | 95/87 |
| 5,391,221 | 2/1995 | Fukushima et al. | 96/102 X |
| 5,431,712 | 7/1995 | Henderson et al. | 96/102 X |
| 5,467,635 | 11/1995 | Nakagawa et al. | 95/19 X |
| 5,531,959 | 7/1996 | Johnson et al. | 96/102 X |
| 5,545,252 | 8/1996 | Hinshaw et al. | 96/102 X |
| 5,567,227 | 10/1996 | Henderson | 95/22 |

Primary Examiner—Robert Spitzer
Attorney, Agent, or Firm—Majestic, Parsons, Siebert & Hsue P.C.

[57] ABSTRACT

A gas chromatograph has a control unit which normally carries out a pressure control so as to keep the pressure inside the vaporization chamber at a specified target level while the flow rate of a carrier gas into the vaporization chamber is kept constant. When a liquid sample is injected to cause a sudden rise in the pressure, the normal pressure control is temporarily stopped, say, for keeping the split ratio unchanged. In order to keep unchanged the retention time for components being analyzed although the pressure inside the vaporization chamber rises, the target value for the pressure control is reduced for an appropriate length of time after the temporary stopping of pressure control is discontinued.

11 Claims, 4 Drawing Sheets

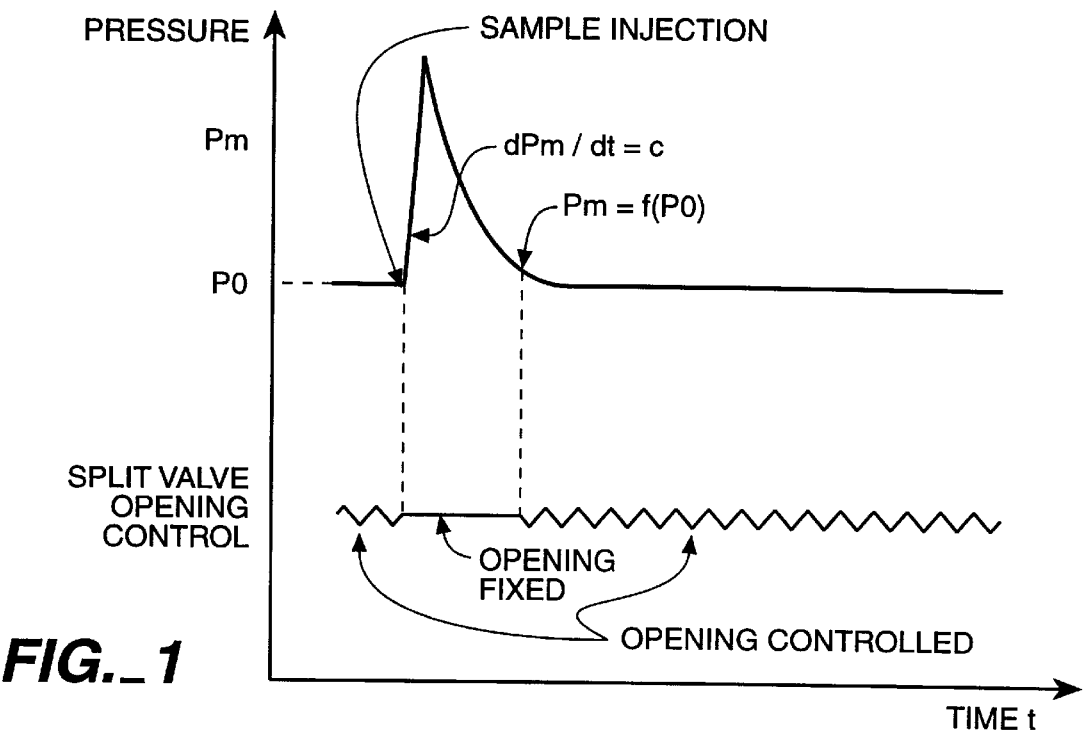
FIG._1
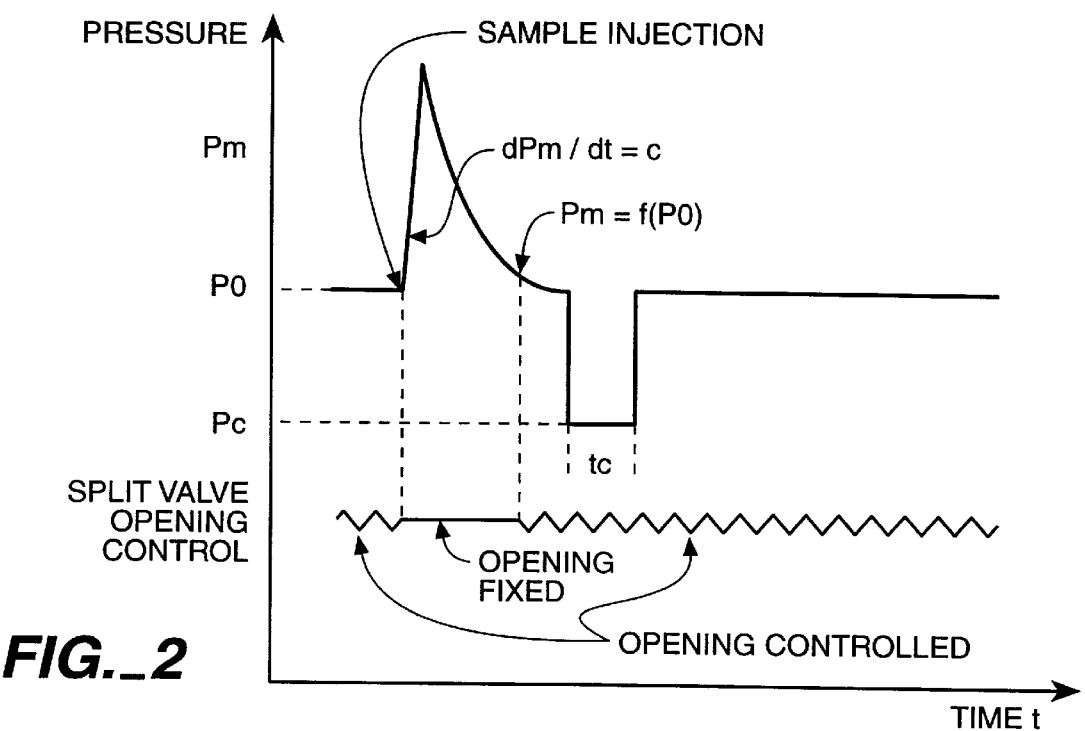
FIG._2

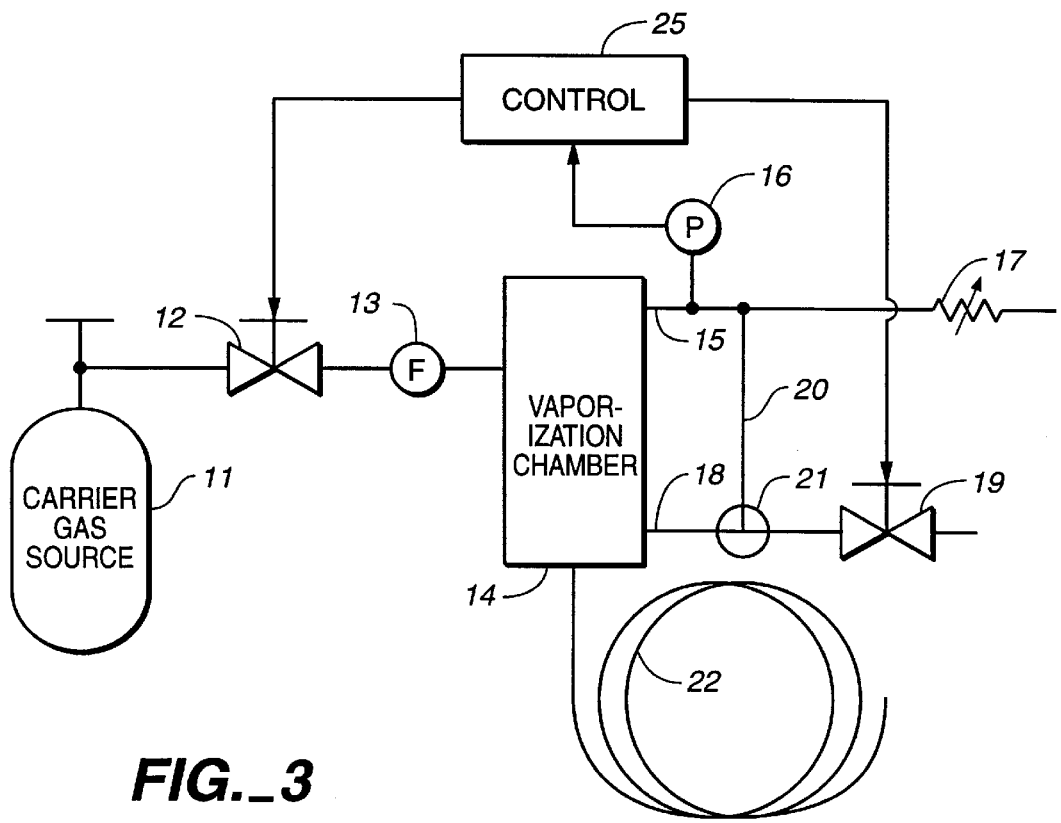
FIG._3
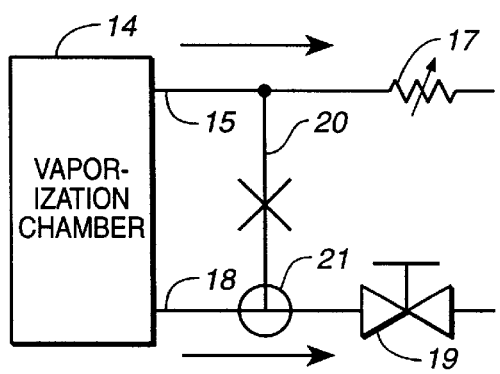
FIG._4A
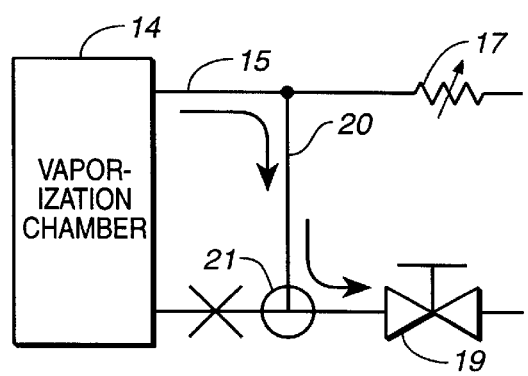
FIG._4B

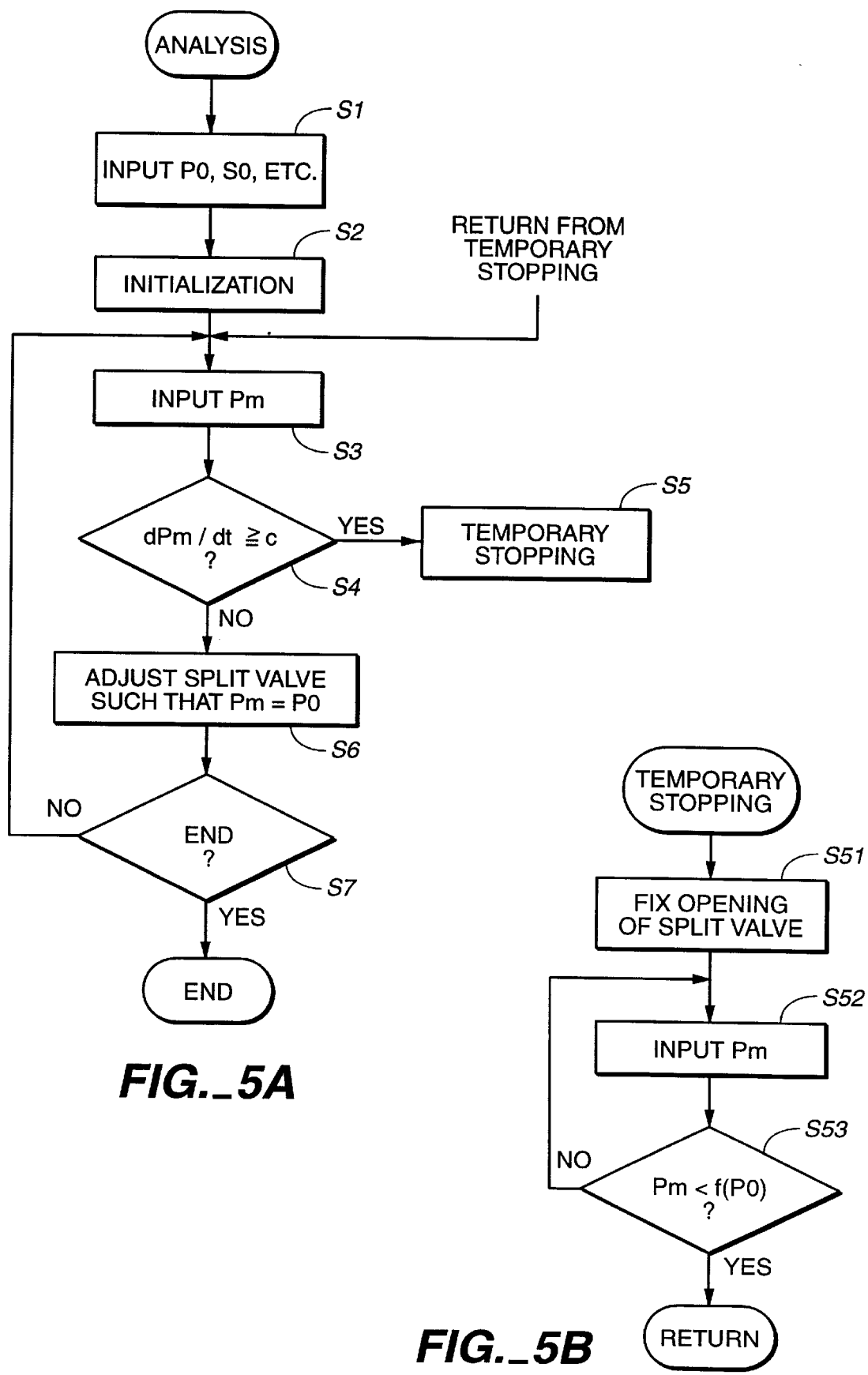
FIG._5A
FIG._5B

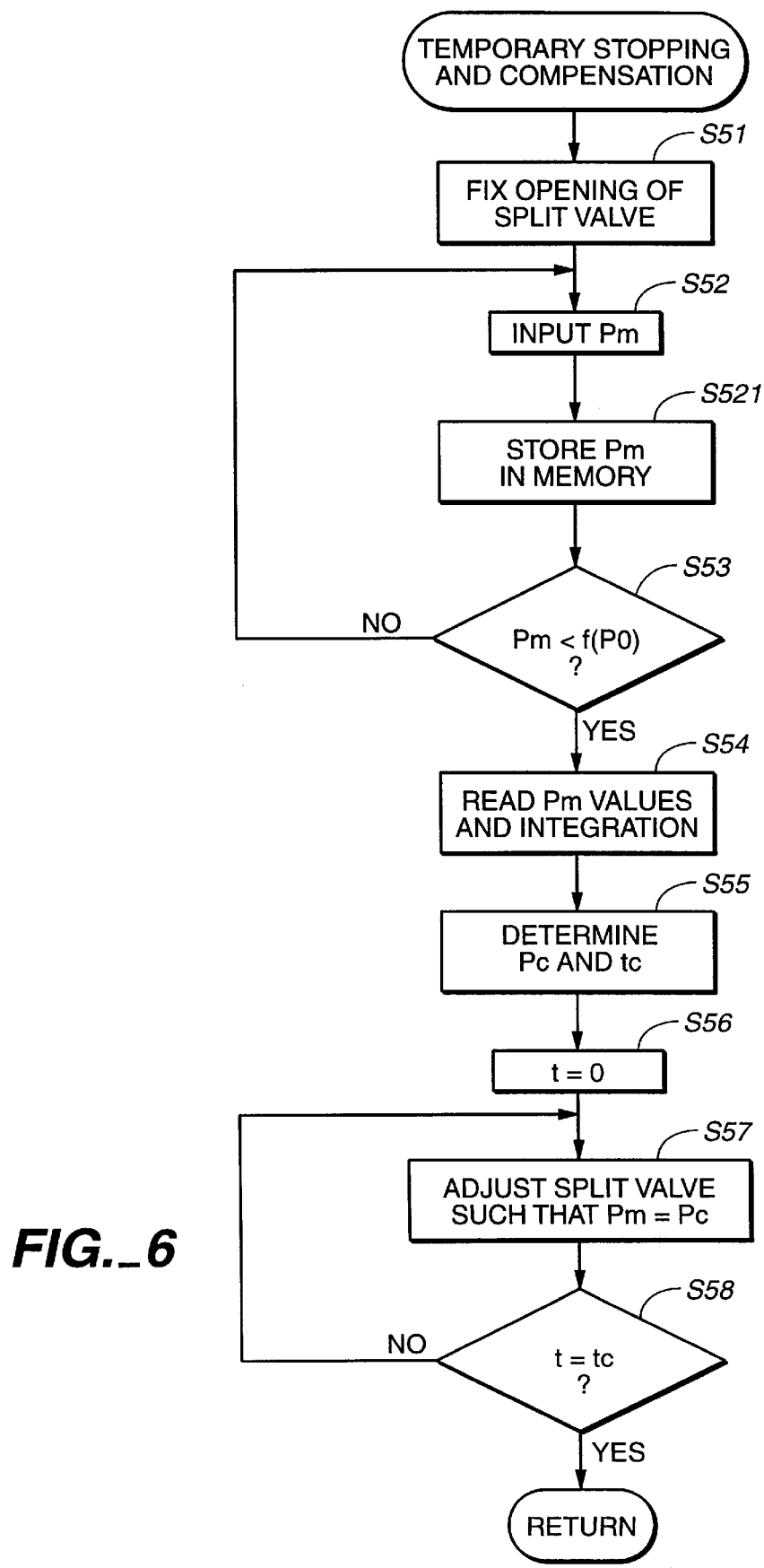
FIG._6

GAS CHROMATOGRAPH AND METHOD OF OPERATING SAME

BACKGROUND OF THE INVENTION

This invention relates to a gas chromatograph for injecting a liquid sample into a sample vaporization chamber to have it vaporized and sending it to a column. More particularly, this invention relates to an improved method of controlling the operation of such a gas chromatograph.

When a gas chromatograph is used for carrying out a split analysis, its control unit not only controls a carrier gas flow control valve such that a carrier gas can be supplied to its sample vaporization chamber at a constant flow rate, but also adjusts the opening of a split valve such that the pressure inside the sample vaporization chamber will stay constant. Thus, the split ratio will remain constant, the pressure at the column entrance can be kept at a specified level and hence a chromatographic process with good reproducibility can be carried out. In the case of a splitless analysis, or an analysis for total amount, a septum purge route will be connected to the split valve, but it is the same as in the case of a split analysis in that the split valve must be controlled to keep a constant pressure inside the sample vaporization chamber.

When a syringe is used to inject a liquid sample into the sample vaporization chamber, the liquid sample is atomized as it is ejected out of the tip of its needle and vaporized immediately by the heat of a heater provided around the sample evaporation chamber, undergoing a significant expansion in volume. In chromatography, it is desirable to keep the peak width as small as possible in order to obtain a high degree of accuracy in the analysis. For this reason, the liquid sample is injected at a high speed, but the pressure inside the vaporization chamber increases rapidly by the volume expansion of the liquid sample immediately after its injection. As explained above, the control unit responds to this situation by increasing the opening of the split valve in order to lower the pressure inside the sample vaporization chamber. When a split analysis is being carried out, however, this has the undesirable effect of causing a change in the split ratio. Since a more than specified amount of the sample is thereby discharged through the split flow route, a correct analysis may not be achievable. In the case of a splitless analysis, too, there is the possibility of the sample being discharged through the septum purge route, adversely affecting the accuracy of the analysis.

SUMMARY OF THE INVENTION

It is therefore an object of this invention to obviate situations as described above by providing an improved gas chromatograph capable of preventing problems in the control of pressure inside the sample vaporization chamber when a liquid sample is injected.

A gas chromatograph embodying this invention, with which the above and other objects can be achieved, may be characterized as comprising a carrier gas flow rate adjusting means for controlling the flow rate of the carrier gas which is supplied into the sample vaporization chamber, a pressure detector for measuring the pressure inside the sample vaporization chamber, a pressure control means for keeping the pressure of sample vaporization chamber constant, and a flow rate control means for keeping the flow rate constant for the carrier gas being supplied into the sample vaporization chamber, normally controlling the pressure controlling means so as to keep the pressure inside the sample vaporization chamber constant but temporarily stopping this pressure control immediately after a liquid sample is injected.

The pressure control means may preferably include a memory device for storing the measured pressure values inside the sample vaporization chamber when the pressure control is temporarily stopped, and a target changing means for changing the target value for the pressure control on the basis of the pressure values stored in the memory device.

The pressure control means causes the carrier gas to be supplied into the sample vaporization chamber at a constant flow rate by means of the carrier gas flow rate adjusting means. Under normal circumstances, the pressure control means keeps monitoring the pressure inside the sample vaporization chamber as outputted from the pressure detector and controls the pressure adjusting means such that the detected pressure will remain at a specified normal target level (P0), which may be constant or variable, depending on the program. The pressure at the entrance to the column is thereby adjusted to P0 while a desired gas chromatographic process is carried out such that a chromatogram with high reproducibility can be obtained.

When a liquid sample is injected into the sample vaporization chamber at the beginning of an analysis, however, the pressure inside the sample vaporization chamber rises suddenly, as explained above. If the pressure control as described above is effected in this situation, the vaporized sample is discharged through the split flow route more than necessary and the desired split ratio fails to be obtained. According to this invention, therefore, the normal pressure control as described above is temporarily stopped immediately after the injection of the liquid sample. What is herein meant by "temporarily stopping pressure control" is to stop the pressure control whereby the flow rate of the discharge gas is varied on the basis of the detected pressure value and the resistance in the split flow route is fixed to its value immediately before this temporary stopping. With the chromatograph thus operated, the split ratio at the time of a split analysis can be maintained at the specified value throughout the period of analysis and an accurate analysis becomes possible.

The starting time for temporarily stopping the pressure control may be determined by the pressure control means on the basis of the pressure value (or its change) inside the sample vaporization chamber. When an automatic sample injector is used for the injection of the liquid sample, a signal therefrom indicative of the start of the sample injection may be relied upon. When the liquid sample is injected manually, the starting time may be decided upon by the user's manual operation of a starting button or the like. Similarly, the time to end the temporary stopping of the pressure control may be determined by the pressure control means on the basis of the lowering of the pressure inside the sample vaporization chamber, or it may be after a predetermined length of time has passed.

If the pressure control is thus stopped temporarily, the pressure inside the sample vaporization chamber rises from the specified normal target level P0. As the pressure at the entrance to the column thus increases, the retention time for each component of gas chromatography becomes shorter. Because this change in the retention time varies, depending of the injected amount of the sample, problems arise as to the reproducibility of the analysis and the identification of each component. According to a preferred embodiment of this invention, the pressure values (or the pressure change with time) inside the sample vaporization chamber, while the pressure control is stopped, are stored in the memory device and, when the normal pressure control is resumed, the target pressure level for the resumed pressure control is changed according to the stored pressure values (or the pressure change with time). Explained more in detail, the target value for the pressure control is lowered after the end of the temporary stopping of the pressure control since the pressure inside the sample vaporization chamber increases while the pressure control is stopped. With the target value thus lowered from the specified normal target level P0, the retention time of each component shifts in the direction of longer time. Thus, the retention time of each component can be rendered unchanged if the target level of the pressure control is lowered appropriately, depending on the pressure values which have been stored.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a graph which shows the changes in the pressure inside the sample vaporization chamber and the opening of the split valve of a gas chromatograph controlled according to a first embodiment of this invention;

FIG. 2 is a graph which shows the changes in the pressure inside the sample vaporization chamber and the opening of the split valve of the gas chromatograph controlled according to a second embodiment of this invention;

FIG. 3 is a schematic drawing for showing the structure of a gas chromatograph embodying this invention;

FIGS. 4A and 4B are flow route diagrams when a split analysis and a splitless analysis are carried out with a gas chromatograph of this invention;

FIGS. 5A and 5B are flow charts of the operation of the gas chromatograph controlled according to the first embodiment of this invention; and FIG. 6 is a flow chart of the operation of the gas chromatograph which is controlled according to the second embodiment of this invention when, and after, its pressure control is stopped.

DETAILED DESCRIPTION OF THE INVENTION

A gas chromatograph which is controlled according to this invention will be described first with reference to FIGS. 1, 3, 5A and 5B. Structurally, as shown in FIG. 3, it is basically the same as prior art apparatus, comprising a carrier gas source 11, a carrier gas flow rate control valve 12, a carrier gas flow detector (F) 13, a sample vaporization chamber 14, a septum purge flow route 15 including a means 17 for varying the flow resistance therethrough, a pressure detector (P) 16, a split flow route 18, a split valve 19, a connecting route 20 between the septum purge flow route 15 and the split flow route 18, a three-way valve 21 at the junction of the split flow route 18 and the connecting route 20, a column 22, and a control unit 25. The control of its operation by the control unit 25 for a split analysis will be explained first with reference to FIGS. 5A and 5B.

To start, conditions of analysis such as the specified target pressure level P0 at the entrance to the column 22 and the split ratio S0 are inputted (Step S1), say, manually by the user through an input means such as a keyboard. Although the aforementioned conditions of analysis include the column temperature and heaters (not shown) disposed around the sample vaporization chamber are controlled also by the control unit 25, the flow charts of FIGS. 5A and 5B are intended to show only the control of pressure, and other types of control are omitted from the explanation.

Next, various initialization steps are carried out (Step S2) prior to the injection of a liquid sample. This includes the calculation of the gas flow rate for the column 22 from given conditions of analysis as well as from the dimensions of the column 22 such as its inner diameter and length, and the determination of the initial levels of opening of the carrier gas flow rate control valve 12 and the split valve 19 on the basis of this calculated value and the split ratio S0. After these valves 12 and 19 are opened to these initial levels, the carrier gas is actually caused to flow in and the pressure inside the sample vaporization chamber 14 is measured by the pressure detector 16. The carrier gas flow rate control valve 12 and the split valve 19 are then adjusted such that the pressure at the entrance to the column and the split ratio will become P0 and S0, respectively. Thereafter, the flow rate of the carrier gas into the sample vaporization chamber 14 is kept fixed, while the opening of the split valve 19 is adjusted such that the pressure at the entrance to the column 22 can be maintained at the normal target level P0. After the conditions for analysis have thus been set, the control unit 25 outputs a signal indicative of the end of the initialization, allowing the user to start the injection of a liquid sample or an automatic sample injector to start its operation.

After the initialization step is thus completed, the control unit 25 continues to monitor pressure values Pm detected by the pressure detector 16 (Step S3) and controls the opening of the split valve 19 such that Pm=P0 (Step S6). In the meantime, it also keeps checking whether the time-rate of change in Pm (=dPm/dt) exceeds a certain specified maximum value c (Step S4). When the liquid sample is injected, this ratio increases suddenly, as explained above and shown in FIG. 1 (Yes in Step S4), and the normal pressure control as described above by the control unit 25 is temporarily stopped (Step S5).

As the normal pressure control (with the normal target level P0) is temporarily stopped, the opening of the split valve 19 is fixed to the level immediately before (Step S51), as shown in FIG. 5B, thereby preventing the split valve 19 from opening too widely in spite of the sudden rise in the pressure inside the sample vaporization chamber 14 immediately after the injection of the liquid sample. The pressure values Pm measured by the pressure detector 16 are continuously monitored (Step S52) to determine whether the measured pressure value Pm satisfies a specified condition (Step S53). The specified condition may be, for example, that the measured pressure value Pm drops to, or below, a certain value f(P0) specified as a function of the originally set normal target value P0 at the entrance to the column 22 such as f(P0)=1.05P0. If the condition for resuming the normal pressure control has come to be satisfied (YES in Step S53), the control unit 25 returns to Step S3 in the flow chart of FIG. 5A.

After the control unit 25 resumes the normal pressure control, the control in Step S6 is continued until a predetermined condition for ending the control, such as the passing of a specified length of time, is satisfied (YES in Step S7).

Different criteria may be used after the injection of a liquid sample for stopping the normal pressure control. The temporary stopping of the normal pressure control may be started, not necessarily by the time-rate of change in Pm (that is, dPm/dt), but by determining whether the measured pressure value Pm exceeds a certain specified critical value g(P0) given as a function of the original target value P0, such as g(P0)=1.1P0.

As explained above, the pressure inside the sample vaporization chamber 14 increases, as shown in FIG. 1, while the normal pressure control is temporarily stopped after the injection of the liquid sample. As the pressure at the entrance to the column 22 becomes higher, the carrier gas carrying a sample begins to travel through the column 22 at a faster rate, shortening the retention time of each component. According to a second embodiment of this invention, this shortening of the retention time is compensated after the end of the temporary stopping of the pressure control, as will be explained more in detail below with reference to FIGS. 2 and 6.

The flow chart in FIG. 6 is the same as that in FIG. 5B except Step S521 is inserted between Steps S52 and S53 and Steps S54–S58 are inserted after Step S53. Thus, according to the second embodiment of this invention, the detected pressure values Pm are stored in a memory device (not shown), which may be considered to be a part of the control unit 25 (Step S521) while the normal pressure control is stopped. After the condition for resuming the normal pressure control is satisfied (YES in Step S53), a pressure compensation process is carried out first by reading out all the stored pressure values Pm and the sum of the differences {Pm−P0} is calculated (Step S54). This sum (multiplied by the time interval between successive measurements of pressure) is an approximation of the time integral of the pressure increase ($\int${Pm−P0}dt), representing the impulse which has increased the momentum of the gas inside the column. Next, a new target pressure value Pc (smaller than P0) is determined (Step S55), and the pressure control process is carried out for a predetermined period of tc with Pc as the reduced target value (Steps S56–S58), as shown in FIG. 2. The reduced pressure value Pc is determined from the aforementioned momentum increase and the predetermined length of the period tc. With a pressure compensation process thus performed, the increase in the gas momentum inside the column is made up for, and each component in the injected sample leaves the column 22 with a desired retention time.

Although the invention has been described above with reference to a split analysis, this invention is applicable also in a splitless analysis. As shown in FIG. 3, the gas chromatograph is provided with a three-way valve 21 and can carry out both a split analysis and a splitless analysis by switching this three-way valve 21, as shown in FIGS. 4A and 4B. Thus, as explained above, the injected liquid sample can be prevented from being discharged through the septum purge flow route 15 as the opening of the split valve is properly controlled as shown in FIGS. 5A and 5B and the retention time can be held constant by carrying out a pressure compensation process as shown in FIG. 6.

What is claimed is:

1. A method of operating a gas chromatograph for having a liquid sample injected into a vaporization chamber and vaporizing said liquid sample to be sent into a column, said method comprising the steps of:
   adjusting the flow rate of a carrier gas supplied into said vaporization chamber;
   monitoring pressure inside said vaporization chamber;
   normally carrying out a pressure control so as to keep the pressure inside said vaporization chamber at a specified target level while keeping the flow rate of said carrier gas constant;
   temporarily stopping said pressure control for a finite period of time immediately after said liquid sample is injected into said vaporization chamber.

2. The method of claim 1 further comprising the steps of:
   storing measured pressure values inside said vaporization chamber, obtained while said pressure control is temporarily stopped; and
   changing a specified target value for said vaporization chamber to a modified value different from said specified target value for a specified adjustment period of time according to said stored measured pressure values after said finite period and said pressure control is resumed.

3. The method of claim 2 including the steps of estimating from said measured pressure values which have been stored a momentum increase of gas inside said column and determining said modified value and said adjustment period of time so as to compensate for said momentum increase.

4. The method of claim 1 wherein said pressure control is temporarily stopped when the time rate of change in pressure value detected inside said vaporization chamber exceeds a pre-set value.

5. The method of claim 1 herein said finite period is ended when monitored pressure inside said vaporization chamber returns to a specified level.

6. A gas chromatograph for having a liquid sample injected into a vaporization chamber and vaporizing said liquid sample to be sent into a column, said gas chromatograph comprising:
   carrier gas flow rate adjusting means for adjusting the flow rate of a carrier gas supplied into said vaporization chamber;
   a pressure detector for monitoring pressure inside said vaporization chamber;
   pressure adjusting means for adjusting an exhaust gas flow rate out of said vaporization chamber; and
   pressure control means for normally carrying out a pressure control by controlling said pressure adjusting means so as to keep the pressure inside said vaporization chamber at a specified target level, said pressure control means being adapted to temporarily stop said pressure control for a finite period of time immediately after a liquid sample is injected into said vaporization chamber.

7. The gas chromatograph of claim 6 wherein said pressure control means include:
   memory means for storing pressure values measured by said pressure detector while said pressure control is temporarily stopped; and
   target changing means for changing a specified target value for said vaporization chamber to a modified value different from said specified target value for a specified adjustment period of time according to stored pressure values in said memory means after said pressure control means resumes said pressure control after once having stopped said pressure control.

8. The gas chromatograph of claim 7 wherein said target changing means estimates from said stored pressure values in said memory means a momentum increase of gas inside said column and determines said modified value and said adjustment period of time so as to compensate for said momentum increase.

9. The gas chromatograph of claim 6 further comprising a septum purge route connected to said vaporization chamber for allowing a gas to be discharged therefrom, said pressure adjusting means including a split flow route connected to said vaporization chamber for allowing a gas to be discharged therefrom and a split valve disposed in said split flow route, said pressure control means being programmed to effect said pressure control so as to keep the split ratio constant by controlling said split valve.

10. The gas chromatograph of claim 6 wherein said pressure control means stops said pressure control when the time rate of change in pressure value detected by said pressure detector exceeds a pre-set value.

11. The gas chromatograph of claim 6 wherein said finite period is ended when the pressure measured by said pressure detector returns to a specified level which is determined by said pressure control means.

* * * * *